United States Patent [19]

Dooley et al.

[11] Patent Number: 5,610,271

[45] Date of Patent: Mar. 11, 1997

[54] KAPPA RECEPTOR SELECTIVE OPIOID PEPTIDES

[75] Inventors: Colette T. Dooley, San Diego; Richard A. Houghten, Del Mar, both of Calif.

[73] Assignee: Torrey Pines Institute for Molecular Studies, San Diego, Calif.

[21] Appl. No.: 472,219

[22] Filed: Jun. 7, 1995

[51] Int. Cl.$^6$ ............................ A61K 38/07; A61K 38/08; C07K 5/10; C07K 7/06
[52] U.S. Cl. .............................................. 530/328; 530/330
[58] Field of Search .............................. 514/809, 15, 18; 530/302, 328, 330

[56] References Cited

U.S. PATENT DOCUMENTS

| | | | |
|---|---|---|---|
| 4,261,883 | 4/1981 | Smolarsky | 260/112.5 |
| 5,017,689 | 5/1991 | Hruby et al. | 530/327 |
| 5,338,668 | 8/1994 | Yoshikawa et al. | 435/68.1 |
| 5,367,053 | 11/1994 | Dooley et al. | 530/329 |

OTHER PUBLICATIONS

Dooley et al., "Acetalins: Opioid receptor antagonists determined through the use of synthetic peptide combinatorial libraries." *Proc. Natl. Acad. Sci. USA*, 90:10811–10815 (1993).

Dooley et al., "An all D-Amino acid opioid peptide with central analgesic activity from a combinatorial library." *Science*, 266:2019–2022 (1994).

Dooley et al., "Rapid identification of novel opioid peptides from an N-acetylated synthetic combinatorial library." *Regulatory Peptides*, 54:87–88 (1994).

Ostresh et al., "Libraries from libraries: Chemical transformation of combinatorial libraries to extend the range and repertoire of chemical diversity." *Proc. Natl. Acad. Sci. USA*, 91:11138–11142 (1994).

Dooley and Houghten, "The use of positional scanning synthetic peptide combinatorial libraries for the rapid determination of opioid receptor ligands." *Life Science*, 52:1509–1517 (1993).

Erchegyi et al., "Isolation of a novel tetrapeptide with opiate and antiopiate activity from human brain cortex: Tyr-Pro-Trp-Gly-NH$_2$ (Tyr-W-MIF-1) " *Peptides*, 13:623–631 (1992).

Schiller et al., "Unsulfated C-terminal 7-peptide of cholecystokinin: a new ligand of the opiate receptor." *Biochem. and Biophys. Res. Comm.*, 85(4):1332–1338 (1978).

Blondelle et al., "Soluble combinatorial libraries of organic, peptidomimetic and peptide diversities." *Trends in Analytical Chem.*, 14(2):83–92 (1995).

Schiller Peter W., "Development of receptor-specific opioid peptide analogues." *Progress in Medicinal Chem.*, 28:301–340 (1991).

Dooley et al., "Identification of tetrameric opioid peptides from a combinatorial library composed L-, D-and non-proteinogenic amino acids." In *H.L.S. Maia (Ed)*, Peptides 94: Proceedings of the 23rd European Peptide Symposium. Escom, Leides (1995).

Houghten and Dooley, "The use of synthetic peptide combinatorial libraries for the determination of peptide ligands in radio-receptor assays: opioid peptides." *BioMed. Chem Lett.*, 3:405–412 (1993).

Hruby and Gehrig, "Recent developments in the design of receptor specific opioid peptides." *Medicinal Res. Rev.*, 9(3):343–401 (1989).

*Primary Examiner*—Jeffrey E. Russel
*Assistant Examiner*—Gregory P. Ritchie
*Attorney, Agent, or Firm*—Campbell & Flores LLP

[57] ABSTRACT

The present invention provides novel opioid peptides which are selective for the kappa opiate receptor. In one embodiment, the kappa-selective opioid peptides have the general structure Ac-A1-B2-C3-Arg-Tyr-Arg-Tyr-Arg-Arg-Arg-NH$_2$, (SEQ ID NO. 28), wherein A1 is Tyr or Arg, B2 is Arg or Phe, and C3 is Thr, Phe, or Met. In yet other embodiments, the kappa-selective opioid peptides have the general structure (D)Phe-D4-E5-F6 (SEQ ID NO. 29) or (D)Nle-D4-E5-F6 (SEQ ID NO. 30), where in both of these formulae D4 is (D)NapAla or (D)Phe, E5 is (D)Nle, Trp, or (D)Ile, and F6 is (D)Arg or (D)ChAla.

6 Claims, No Drawings

KAPPA RECEPTOR SELECTIVE OPIOID PEPTIDES

BACKGROUND OF THE INVENTION

1. Field of the Invention

The present invention relates generally to the field of peptide chemistry and, more specifically, to novel opioid peptides that can inhibit ligand binding to an opioid receptor.

2. Background Information

There are at least three known subtypes of opioid receptors, mu ($\mu$), delta ($\delta$), and kappa ($\kappa$), to which morphine, the enkephalins, and the dynorphins, respectively, bind. The three receptor subtypes possess analgesic properties. However, the type of pain inhibited and the secondary functions vary with each receptor type. The $\kappa$ receptor is potent in affecting analgesia in response to pain, including chemical stimuli. The $\kappa$ receptor also induces diuresis and sedation and is associated with dysphoric and psychometric effects as well as drug or other physical dependence. The $\mu$ receptor is generally regarded as the one associated with pain relief, respiratory depression, intestinal motility, antidiuresis, an immune response, and drug or other physical dependence. The $\delta$ receptor, on the other hand, is associated with thermal analgesia and, to a lesser extent, respiration and addiction. These differences in the opioid receptor functions encourage the search for drugs which produce analgesia without deleterious side effects.

The use of synthetic peptides has been instrumental in the delineation of these subtypes and in providing analogues that can be used for studying the interactions of ligands specific to these receptor systems in both in vitro and in vivo systems. Certain opioid compounds are agonists (bind to the receptor and produce an effect) while others are antagonists (bind to the receptor but do not produce an effect). Most previously known agonists and antagonists of the opioid receptors are analogues of the enkaphalins and related peptides, including the dynorphins, the dermenkephalins and the casomorphins. The compounds of the present invention have little to no sequence homology with any of these known opioid peptides.

Recent advances in methods for the preparation and screening of large numbers of individual peptides has led to the identification of numerous peptides useful in all areas of biomedical research, including research regarding the interaction of a ligand to the opiate receptor. Both receptor-specific agonists and antagonists are needed as pharmacological tools and as therapeutic agents. Even with these advances, however, basic research and drug discovery has been limited by the availability of the requisite large number of diverse opiate agonists and antagonists required to ascertain the relationship between a ligand for a particular opiate receptor subtype. Thus, a need exists for large numbers of individual peptides for use in biomedical research, including those for the study of opiate ligand-receptor interactions. As well there is a need for opioid peptides which have therapeutic value. This invention satisfies these needs and provides related advantages as well.

SUMMARY OF THE INVENTION

The present invention provides novel opioid peptides which are selective for the $\kappa$ opiate receptor. In one embodiment, the opioid peptides have the general structure Ac-A1-B2-C3-Arg-Tyr-Arg-Tyr-Arg-Arg-Arg-NH$_2$, (SEQ ID NO. 28), wherein A1 is Tyr or Arg, B2 is Arg or Phe, and C3 is Thr, Phe, or Met. In yet other embodiments, the opioid peptides have the general structure (D)Phe-D4-E5-F6 (SEQ ID NO. 29) or (D)Nle-D4-E5-F6 (SEQ ID NO. 30), where in both of these formulae D4 is (D)NapAla or (D)Phe, E5 is (D)Nle, Trp, or (D)Ile, and F6 is (D)Arg or (D)ChAla.

DETAILED DESCRIPTION OF THE INVENTION

The present invention provides novel opioid peptides which are capable of inhibiting the binding of the $\kappa$-selective opioid ligand [$^3$H]-U69,593. In one embodiment, the peptides have the general structure Ac-A1-B2-C3-Arg-Tyr-Arg-Tyr-Arg-Arg-Arg-NH$_2$, (SEQ ID NO. 28), wherein A1 is Tyr or Arg, B2 is Arg or Phe, and C3 is Thr, Phe, or Met. Exemplary peptides encompassed by this formula, include the following: Ac-Tyr-Arg-Thr-Arg-Tyr-Arg-Tyr-Arg-Arg-Arg-NH$_2$ (SEQ ID NO. 1); Ac-Tyr-Arg-Phe-Arg-Tyr-Arg-Tyr-Arg-Arg-Arg-NH$_2$ (SEQ ID NO. 2); Ac-Arg-Phe-Phe-Arg-Tyr-Arg-Tyr-Arg-Arg-Arg-NH$_2$ (SEQ ID NO. 3); Ac-Tyr-Arg-Met-Arg-Tyr-Arg-Tyr-Arg-Arg-Arg-NH$_2$ (SEQ ID NO. 4); and Ac-Arg-Arg-Phe-Arg-Tyr-Arg-Tyr-Arg-Arg-Arg-NH$_2$ (SEQ ID NO. 5).

In another embodiment, the novel peptides are those encompassed by the formula (D)Phe-D4-E5-F6 (SEQ ID NO. 29), wherein D4 is (D)NapAla or (D)Phe, E5 is (D)Nle, Trp, or (D)Ile, and F6 is (D)Arg or (D)ChAla. Exemplary peptides within this embodiment have any one of the following sequences: (D)Phe-(D)NapAla-(D)Nle-(D)Arg (SEQ ID NO. 6); (D)Phe-(D)NapAla-(D)Nle-(D)ChAla (SEQ ID NO. 7); (D)Phe-(D)NapAla-Trp-(D)Arg (SEQ ID NO. 8); (D)Phe-(D)NapAla-Trp-(D)ChAla (SEQ ID NO. 9); (D)Phe-(D)NapAla-(D)Ile-(D)Arg (SEQ ID NO. 10); (D)Phe-(D)NapAla-(D)Ile-(D)ChAla (SEQ ID NO. 11); (D)Phe-(D)Phe-(D)Nle-(D)Arg (SEQ ID NO. 12); (D)Phe-(D)Phe-(D)Nle-(D)ChAla (SEQ ID NO. 13); (D)Phe-(D)Phe-Trp-(D)Arg (SEQ ID NO. 14); (D)Phe-(D)Phe-Trp-(D)ChAla (SEQ ID NO. 15); (D)Phe-(D)Phe-(D)Ile-(D)Arg (SEQ ID NO. 16); and (D)Phe-(D)Phe-(D)Ile-(D)ChAla (SEQ ID NO. 17).

In yet another embodiment of the invention, the peptides have the structure (D)Nle-D4-E5-F6 (SEQ ID NO. 30), wherein D4 is (D)NapAla or (D)Phe, E5 is (D)Nle, Trp, or (D)Ile, and F6 is (D)Arg or (D)ChAla. Exemplary peptides which fall within the scope of this formula include the following sequences: (D)Nle-(D)NapAla-(D)Nle-(D)Arg (SEQ ID NO. 18); (D)Nle-(D)NapAla-(D)Nle-(D)ChAla (SEQ ID NO. 19); (D)Nle-(D)NapAla-Trp-(D)Arg (SEQ ID NO. 20); (D)Nle-(D)NapAla-(D)Ile-(D)Arg (SEQ ID NO. 21); (D)Nle-(D)NapAla-(D)Ile-(D)ChAla (SEQ ID NO. 22); (D)Nle-(D)Phe-(D)Nle-(D)Arg (SEQ ID NO. 23); (D)Nle-(D)Phe-Trp(D)Arg (SEQ ID NO. 24); (D)Nle-(D)Phe-Trp-(D)ChAla (SEQ ID NO. 25); (D)Nle-(D)Phe-(D)Ile-(D)Arg (SEQ ID NO. 26); and (D)Nle-(D)Phe-(D)Ile-(D)ChAla (SEQ ID NO. 27).

The following standard abbreviations are used herein to identify amino acid residues.

| Amino Acid | Three-letter Abbreviation | One-letter Symbol |
| --- | --- | --- |
| Alanine | Ala | A |
| Arginine | Arg | R |
| CyclohexylAlanine | ChAla | — |
| Isoleucine | Ile | I |
| Leucine | Leu | L |
| Methionine | Met | M |

| Amino Acid | Three-letter Abbreviation | One-letter Symbol |
|---|---|---|
| Naphthylalanine | NapAla | — |
| NorLeucine | Nle | — |
| Phenylalanine | Phe | F |
| Threonine | Thr | T |
| Tryptophan | Trp | W |
| Tyrosine | Tyr | Y |

The amino acids are indicated by these commonly known codes as provided above and (D) designates an amino acid having the "D" configuration, as opposed to the naturally occurring L-amino acids. Where no specific configuration is indicated, one skilled in the art would understand the amino acid to be an (L)-amino acid.

One skilled in the art would know that one or more amino acids within the exemplified peptides could be modified or substituted, as for example, by a conservative amino acid substitution of one or more of the specific amino acids shown in the exemplified peptides. A conservative amino acid substitution change can include, for example, the substitution of one basic amino acid for another basic amino acid, of one hydrophobic amino acid for another hydrophobic amino acid or other conservative substitutions well known in the art, including the use of non-naturally occurring amino acids, such as ornithine (Orn) or homoArginine (homoArg) for Arg.

In addition to the above types of modifications or substitutions, a mimic of one or more amino acids, otherwise known as a peptide mimetic or peptidomimetic, can also be used. As used herein, the term "mimic" means an amino acid or an amino acid analog that has the same or similar functional characteristic of an amino acid. Thus, for example, a (D)arginine analog can be a mimic of (D)arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide.

The substitution of amino acids by non-naturally occurring amino acids and peptidomimetics as described above can enhance the overall activity or other properties of an individual peptide based on the modifications to the side chain functionalities. For example, these types of alterations to the exemplified peptides can enhance the peptide's stability to enzymatic breakdown or increase biological activity or decrease immunogenicity.

One skilled in the art, using the above formulae, can easily synthesize the peptides of this invention. Standard procedures for preparing synthetic peptides are well known in the art. The novel opioid peptides can be synthesized using the solid phase peptide synthesis (SPPS) method of Merrifield (*J. Am. Chem. Soc.*, 85:2149 (1964), which is incorporated herein by reference) or modifications of SPPS, or the peptides can be synthesized using standard solution methods well known in the art (see, for example, Bodanzsky, M., *Principles of Peptide Synthesis* 2nd revised ed. (Springer-Verlag, 1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

In the exemplified peptides, "Ac" indicates an acetyl group at the amino terminus and "$NH_2$" means an amide group is at the carboxy terminus. Peptides can be manipulated, for example, while still attached to a resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus such as methods for acetylation of the N-terminus or methods for amidation of the C-terminus are well known in the art.

A newly synthesized peptide can be purified using a method such as reverse phase high performance liquid chromatography (RP-HPLC), chromatofocusing, or other methods of separation based on the size or charge of the peptide, or by immuno-purification techniques. Furthermore, the purified peptide can be characterized using these and other well known methods such as amino acid analysis and mass spectrometry.

After manufacture, the peptides can be assayed for $\kappa$ receptor binding activity using the $\kappa$ radioreceptor assay as provided in Example I. For additional data on the specificity of the peptides, results from a $\kappa$ radioreceptor assay can be compared with those of $\mu$ and $\delta$ radioreceptor assays as provided in Example II. To test the in vitro agonist or antagonist activity of the peptides, well known in vivo assays, such as the guinea-pig ileum assay as described in Example III can be routinely performed. In addition, several other reliable in vivo tests are known in the art which are useful for testing the opioid peptides and compositions of the present invention. Exemplary tests include the mouse tail-flick, tail-pinch and HCl writhing tests, as well as the rat warm-plate and hot plate assays, and rat tail-immersion, tail-flick and air writhing assays, all of which are described in Vonvoigtlander et al., *Journal of Pharmacology and Experimental Therapeutics*, 224(1):7–12 (1983), which is incorporated herein by reference. One of the more commonly used assays of those described above, the mouse tail-flick in vivo animal model, is also described by Dixon et al., *Drug Res.*, 27:1968 (1977), Jiang et al., *J. Pharmacol. Exp. Ther.*, 262:526 (1992), and Dooley et al., *Science*, 266:2019 (1994), all of which are incorporated herein by reference.

Because the peptides of the present invention bind to the $\kappa$ receptor, they can be used in in vitro assays to study the opiate receptor subtypes. For example, in a sample receptor of unknown type or origin, the peptides, after being labeled with a detectable marker such as a radioisotope, can be contacted with the receptor sample under conditions which specifically favor binding to a particular receptor subtype, such as the κ subtype. Unbound receptor and peptide can be removed, for example, by washing with a saline solution, and bound receptor can then be detected using methods well known to those skilled in the art. Therefore, the peptides of the present invention are useful in vitro for the diagnosis of relevant opioid receptor subtypes, and in particular the κ type, in brain and other tissue samples.

In addition to their utility in in vitro screening methods, the peptides are also useful in vivo. For example, the opioid peptides can be used in vivo diagnostically to localize opioid receptor subtypes. The peptides are also useful as drugs, namely as analgesics, or to treat pathologies associated with other compounds which interact with the opioid receptor system. For example, it can be envisioned that these peptides can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many peptides do not readily cross the blood-brain barrier and, therefore, elicit no central effect, the subject peptides can have value in blocking the periphery effects of morphine, such as constipation and pruritus.

The novel peptides claimed can be incorporated into pharmaceutical compositions, Pharmaceutically acceptable carriers are well known in the art and include aqueous solutions such as physiologically buffered saline or other buffers or solvents or vehicles such as glycols, glycerol, oils such as olive oil or injectable organic esters. A pharmaceutically acceptable carrier can contain physiologically acceptable compounds that act, for example, to stabilize the opioid peptide or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on the particular physiochemical characteristics of the specific opioid peptide.

Methods of administering a pharmaceutical are well known in the art and include but are not limited to administration orally, intravenously, intramuscularly or intraperitoneal. Administration can be effected continuously or intermittently and will vary with the subject and is dependent on the type of treatment and potency of the peptide used.

The following examples are intended to illustrate but not limit the present invention.

EXAMPLE I

Identification Of Kappa Selective Opioid Peptides By Radioreceptor Assay

This example describes the identification of individual peptides as inhibitors of the κ-selective ligand, [$^3$H]-U69,593. Individual peptides were identified as capable of inhibiting [$^3$H]-U69,593 by a radioreceptor assay.

Synthetic combinatorial libraries (SCLs) made up of mixtures of tens of millions of different peptides can be used to rapidly identify individual, active compounds. Since the libraries are in solution (i.e., not attached to a bead, pin, phage, glass, etc.) they can be screened in virtually any assay system. All opioid peptides were initially prepared and contained within a positional scanning synthetic combinatorial library (PS-SCL). The libraries were used in conjunction with an iterative selection process to identify individual peptides capable of inhibiting [$^3$H]-U69,593 in the radioreceptor assay.

As detailed below, the peptide libraries were screened in a radioreceptor assay using rat brain homogenates and [$^3$H]-U69,593 as radioligand and $Ic_{50}$ values determined for peptides which significantly inhibited the binding of [$^3$H]-U69,593.

Radioreceptor Assays Selective For The Kappa Receptor

Guinea pig brains, frozen in liquid nitrogen, were obtained from Harlan Bioproducts for Science (Indianapolis, Ind.). Frozen brains were thawed, the cerebella and cortex were removed and weighed. The combined cortex and cerebella were homogenized in 40 ml Tris-HCl buffer (50 mM, pH 7.4, 4° C.) containing 100 μM phenylmethylsulfonyl fluoride (PMSF) 5 mM $MgCl_2$ and 1 mg/ml bovine serum albumin (BSA) and centrifuged (39000×g) (Model J2-HC; Beckman Instruments, Fullerton, Calif.) for 10 min at 4° C. The pellets were resuspended in fresh Tris-HCl buffer and incubated at 37° C. for 40 min. Following incubation, the suspensions were centrifuged as above, the resulting pellets resuspended in 100 volumes of Tris buffer and the suspensions combined. Membrane suspensions were prepared and used in the same day. Protein content of the crude homogenates ranged from 0.1–0.3 mg/ml as determined using the method described by Bradford in *Anal. Biochem.* 72:248–254 (1976), which is incorporated herein by reference.

Binding assays were carried out in polypropylene tubes. Each tube contained 3 nM of the κ-selective ligand [$^3$H]-U69,593 (specific activity 62 Ci/mmol)(Amersham; Arlington Heights, Ill.), peptide mixture (a range of $3\times10^4$ to $3\times10^5$M concentration for individual peptides in the mixture), and tissue homogenates prepared from guinea pig brains (cortex and cerebellum) using Tris buffer containing 100 μM PMSF, 5 mM $MgCl_2$ and 1 mg/ml BSA, pH 7.4. Assay tubes were incubated for 2.5 hr at 25° C. The reaction was terminated by filtration through GF-B filters (Wallac, Gaithesburg, Md.). The filters were subsequently washed with 6 ml Tris-HCl buffer at 4° C. Bound radioactivity was counted on a Beta-plate Liquid Scintillation Counter (Life Technologies, Gaithersburg, Md.) and expressed in counts per minute (cpm). Standard curves were prepared using 0.05–6300 nM naloxone (Sigma, St. Louis, Mo.). Competitive inhibition assays were performed as above using serial dilutions of the peptide mixtures. $IC_{50}$ values were then calculated using the software GRAPHPAD (ISI, San Diego, Calif.). The average standard deviation for $IC_{50}$ values was ±20%.

$IC_{50}$ values of less than 1000 nM are indicative of highly active opioid peptides which bind to the κ receptor, with particularly active compounds having $IC_{50}$ values of 100 nM or less, and the most active compounds with values of less than 10 nM.

Opioid peptides identified from the assay screening of one SCL have the general structure Ac-A1-B2-C3-Arg-Tyr-Arg- Tyr-Arg-Arg-Arg-NH$_2$, (SEQ ID NO. 28), wherein A1 is Tyr or Arg, B2 is Arg or Phe, and C3 is Thr, Phe, or Met. IC$_{50}$ values of peptides falling within the scope of this formula are provided in Table 1.

TABLE 1

Ac—A1—B2—C3—Arg—Tyr—Arg—Tyr—Arg—Arg—Arg—NH$_2$
(SEQ ID NO. 28)

| SEQ ID NO. | PEPTIDE | IC$_{50}$ (nM) |
|---|---|---|
| 1 | Ac—Y—R—T—R—Y—R—Y—R—R—R—NH$_2$ | 10 |
| 2 | Ac—Y—R—F—R—Y—R—Y—R—R—R—NH$_2$ | 18 |
| 3 | Ac—R—F—F—R—Y—R—Y—R—R—R—NH$_2$ | 22 |
| 4 | Ac—Y—R—M—R—Y—R—Y—R—R—R—NH$_2$ | 36 |
| 5 | Ac—R—R—F—R—Y—R—Y—R—R—R—NH$_2$ | 142 |

Also identified as κ-selective peptides are those of the general formula (D)Phe-D4-E5-F6 (SEQ ID NO. 29), wherein D4 is (D)NapAla or (D)Phe, E5 is (D)Nle, Trp, or (D)Ile, and F6 is (D)Arg or (D)ChAla. Table 2 provides the respective IC$_{50}$ values for each of the peptides within this formula.

TABLE 2

(D)Phe—D4—E5—F6 (SEQ ID NO. 29)

| SEQ ID NO. | PEPTIDE | IC$_{50}$ (nM) |
|---|---|---|
| 6 | (D)Phe—(D)NapAla—(D)Nle—(D)Arg | 0.2 |
| 7 | (D)Phe—(D)NapAla—(D)Nle—(D)ChAla | 8 |
| 8 | (D)Phe—(D)NapAla—Trp—(D)Arg | 7584 |
| 9 | (D)Phe—(D)NapAla—Trp—(D)ChAla | 24984 |
| 10 | (D)Phe—(D)NapAla—(D)Ile—(D)Arg | 0.7 |
| 11 | (D)Phe—(D)NapAla—(D)Ile—(D)ChAla | 86 |
| 12 | (D)Phe—(D)Phe—(D)Nle—(D)Arg | 0.8 |
| 13 | (D)Phe—(D)Phe—(D)Nle—(D)ChAla | 3 |
| 14 | (D)Phe—(D)Phe—Trp—(D)Arg | 4953 |
| 15 | (D)Phe—(D)Phe—Trp—(D)ChAla | 52430 |
| 16 | (D)Phe—(D)Phe—(D)Ile—(D)Arg | 2 |
| 17 | (D)Phe—(D)Phe—(D)Ile—(D)ChAla | 169 |

Peptides of the general formula (D)Nle-D4-E5-F6 (SEQ ID NO. 30), wherein D4 is (D)NapAla or (D)Phe, E5 is (D)Nle, Trp, or (D)Ile, and F6 is (D)Arg or (D)ChAla were also identified as inhibitors of [$^3$H]-U69,593. The IC$_{50}$ values of peptides within this formula are provided in Table 3 below.

TABLE 3

(D)Nle—D4—E5—F6 (SEQ ID NO. 30)

| SEQ ID NO. | PEPTIDE | IC$_{50}$ (nM) |
|---|---|---|
| 18 | (D)Nle—(D)NapAla—(D)Nle—(D)Arg | 3 |
| 19 | (D)Nle—(D)NapAla—(D)Nle—(D)ChAla | 6 |
| 20 | (D)Nle—(D)NapAla—Trp—(D)Arg | 743 |
| 21 | (D)Nle—(D)NapAla—(D)Ile—(D)Arg | 2 |
| 22 | (D)Nle—(D)NapAla—(D)Ile—(D)ChAla | 42 |
| 23 | (D)Nle—(D)Phe—(D)Nle—(D)Arg | 10 |
| 24 | (D)Nle—(D)Phe—Trp—(D)Arg | 10985 |
| 25 | (D)Nle—(D)Phe—Trp—(D)ChAla | 42846 |
| 26 | (D)Nle—(D)Phe—(D)Ile—(D)Arg | 16 |
| 27 | (D)Nle—(D)Phe—(D)Ile—(D)ChAla | 1447 |

The results of Tables 1 through 3 above provide three structurally unique series of opioid peptides which are all selective for the κ opioid receptor.

EXAMPLE II

Kappa Receptor Specificity of Opioid Peptides

This example demonstrates how to obtain additional data on the specificity of the novel opioid peptides for the κ receptors as compared to the μ and δ opiate receptors.

Individual peptides can be synthesized by procedures well known in the art as discussed above. The activity of the individual, synthesized peptides in radioreceptor assays selective for the μ and δ receptors, as detailed below, can be compared to the results of the radioreceptor assay selective for the κ receptors from Example I.

Radioreceptor assays selective for μ receptors can be performed using rat brain homogenates as above. Sample polypropylene tubes are prepared so as to contain approximately 0.5 ml of membrane suspension, 3 nM of the μ-selective opioid peptide [$^3$H]-DAMGO (specific activity 36 Ci/mmol), 0.08 mg/ml peptide mixture and Tris-HCl buffer in a total volume of 0.65 ml. Assay tubes are generally incubated for 60 min at 25° C. and the reaction terminated by filtration through, for example, GF-B filters. The filters are subsequently washed with 6 ml Tris-HCl buffer at 4° C. Bound radioactivity is then counted on, for example, a Beta-plate Liquid Scintillation Counter (Life Technologies, Gaithersburg, Md.) and expressed in counts per minute (cpm). Standard curves can be determined by incubation of [$^3$H]-DAMGO in the presence of 0.13–3900 nM of unlabeled DAMGO.

Radioreceptor assays selective for δ receptors can be performed using rat brain homogenates as above and [$^3$H]-naltrindole (0.5 nM, specific activity 34.7 Ci/mmol) as radioligand in Tris buffer containing 100 μM phenylmethylsulfonyl fluoride (PMSF), 5 mM MgCl$_2$ and 1 mg/ml bovine serum albumin (BSA), pH 7.4. Samples are generally incubated for 2.5 hr. Standard curves are prepared using 0.10–3200 nM [$^3$H]-D-Pen2, Pen$_5$]-enkephalin ([$^3$H]-DPDPE). All other steps are as described above.

Tritiated ligands, [$^3$H]-DAMGO and [$^3$H]-DPDPE. can be obtained from the National Institute on Drug Abuse (NIDA) repository, as prepared by Multiple Peptide Systems (San Diego, Calif.), and [$^3$H]-naltrindole from DuPont NEN Research Products (Los Angeles, Calif.). The average standard deviation for IC$_{50}$ values was ±20%.

The comparative data in the respective κ, μ, and δ radioreceptor assays can further demonstrate the selectivity of the novel opioid peptides for the κ receptors over the μ and δ opiate receptors.

EXAMPLE III

Kappa Receptor Agonist or Antagonist Activity by Guinea-Pig Ileum Assay

This example demonstrates that certain novel opioid peptides can be identified as agonists or antagonists of the κ receptor by the guinea-pig ileum assay.

Guinea-Pig Ileum Assay

A guinea-pig ileum (GPI) bioassay can be carried out to determine whether a peptide is an opioid agonist. Again, such information cannot be determined from the above-described radioreceptor binding assays.

The GPI assay (Kosterlitz et al., *Br. J. Pharam.* 39:398–418 (1970), which is incorporated herein by reference), is one of the most widely used assays for the determination of opioid activities in vitro. The assay is based on the ability of opioid agonists to inhibit electrically stimulated contraction in tissue. GPI is not a "clean" assay insofar as the ileum preparation contains both μ and κ receptors. However, κ receptor mediated effects in the GPI can be distinguished from μ receptor mediated effects by determining $K_e$ values for the antagonist (κ effects: $K_e$~20–30 nM; μ effects: $K_e$~1–3 nM) or by blocking μ receptors with a specific μ antagonist, such as CTAP ((D)Tca-Cys-Tyr-(D)Trp-Arg-Thr-Pen-Thr-$NH_2$, wherein Tca is a cyclic (D)Trp analogue).

The guinea pigs are killed by decapitation, the ileum removed and longitudinal muscle-myenteric plexus preparations placed in Krebs solution (NaCl 118 mM, KCl 4.75 mM, $NaH_2PO_4$ 1 mM, $NaHCO_3$ 25 mM, $MgSO_4$ 1.2 mM, glucose 11 mM and $CaCl_2$ 2.5 mM). The solution is gassed with 95% $O_2$ and 5% $CO_2$ and maintained at 37° C. The tissue is suspended under a final tension of 1 g in a 10 ml organ bath and stabilized for 1 hr. Electrical stimulation via a straight platinum electrode is applied, 0.4 ms pulses of supra maximal voltage, delivered at a rate of 0.1 Hz. Isometric contractions are then measured via strain gauge force transducers and recorded on stripchart recorders.

Although the invention has been described with reference to the examples provided above, it should be understood that various modifications can be made by those skilled in the art without departing from the invention. Accordingly, the invention is set out in the following claims.

---

We claim:
1. A peptide having the structure:
Ac-A1-B2-C3-Arg-Tyr-Arg-Tyr-Arg-Arg-NH$_2$, (SEQ ID NO. 28)
wherein A1 is Tyr or Arg;
B2 is Arg or Phe; and
C3 is Thr, Phe, or Met.
2. The peptide of claim 1, having a sequence selected from the group consisting of:
Ac-Tyr-Arg-Thr-Arg-Tyr-Arg-Tyr-Arg-Arg-NH$_2$ (SEQ ID NO. 1);
Ac-Tyr-Arg-Phe-Arg-Tyr-Arg-Tyr-Arg-Arg-NH$_2$ (SEQ ID NO. 2);
Ac-Arg-Phe-Phe-Arg-Tyr-Arg-Tyr-Arg-Arg-NH$_2$ (SEQ ID NO. 3);
Ac-Tyr-Arg-Met-Arg-Tyr-Arg-Tyr-Arg-Arg-NH$_2$ (SEQ ID NO. 4); and
Ac-Arg-Arg-Phe-Arg-Tyr-Arg-Tyr-Arg-Arg-NH$_2$ (SEQ ID NO. 5).
3. A peptide having the structure:
(D)Phe-D4-E5-F6 (SEQ ID NO. 29),
wherein D4 is (D) NapAla or (D) Phe;
E5 is (D)Nle, Trp, or (D)Ile; and
F6 is (D)Arg or (D)ChAla.
4. The peptide of claim 3, having a sequence selected from the group consisting of:
(D)Phe-(D)NapAla-(D)Nle-(D)Arg (SEQ ID NO. 6);
(D)Phe-(D)NapAla-(D)Nle-(D)ChAla (SEQ ID NO. 7);
(D)Phe-(D)NapAla-Trp-(D)Arg (SEQ ID NO. 8);
(D)Phe-(D)NapAla-Trp-(D)ChAla (SEQ ID NO. 9);
(D)Phe-(D)NapAla-(D)Ile-(D)Arg (SEQ ID NO. 10);
(D)Phe-(D)NapAla-(D)Ile-(D)ChAla (SEQ ID NO. 11);
(D)Phe-(D)Phe-(D)Nle-(D)Arg (SEQ ID NO. 12);
(D)Phe-(D)Phe-(D)Nle-(D)ChAla (SEQ ID NO. 13);
(D)Phe-(D)Phe-Trp-(D)Arg (SEQ ID NO. 14);
(D)Phe-(D)Phe-Trp-(D)ChAla (SEQ ID NO. 15);
(D)Phe-(D)Phe-(D)Ile-(D)Arg (SEQ ID NO. 16); and
(D)Phe-(D)Phe-(D)Ile-(D)ChAla (SEQ ID NO. 17).
5. A peptide having the structure:
(D) Nle-D4-E5-F6 (SEQ ID NO. 30),
wherein D4 is (D) NapAla or (D) Phe;
E5 is (D)Nle, Trp, or (D)Ile; and
F6 is (D)Arg or (D)ChAla.
6. The peptide of claim 5, having a sequence selected from the group consisting of:
(D)Nle-(D)NapAla-(D)Nle-(D)Arg (SEQ ID NO. 18);
(D)Nle-(D)NapAla-(D)Nle-(D)ChAla (SEQ ID NO. 19);
(D)Nle-(D)NapAla-Trp-(D)Arg (SEQ ID NO. 20);
(D)Nle-(D)NapAla-(D)Ile-(D)Arg (SEQ ID NO. 21);
(D)Nle-(D)NapAla-(D)Ile-(D)ChAla (SEQ ID NO. 22);
(D)Nle-(D)Phe-(D)Nle-(D)Arg (SEQ ID NO. 23);
(D)Nle-(D)Phe-Trp-(D)Arg (SEQ ID NO. 24);
(D)Nle-(D)Phe-Trp-(D)ChAla (SEQ ID NO. 25);
(D)Nle-(D)Phe-(D)Ile-(D)Arg (SEQ ID NO. 26); and
(D)Nle-(D)Phe-(D)Ile-(D)ChAla (SEQ ID NO. 27).

* * * * *

UNITED STATES PATENT AND TRADEMARK OFFICE
CERTIFICATE OF CORRECTION

PATENT NO. : 5,610,271
DATED : Mar. 11, 1997
INVENTOR(S) : Dooley et al.

It is certified that error appears in the above-identified patent and that said Letters Patent is hereby corrected as shown below:

In column 1, before "BACKGROUND OF THE INVENTION" please insert --This invention was made with government support under grant DA09410 awarded by the National Institute on Drug Abuse, National Institutes of Health. The government has certain rights in the invention.--.

In column 1, line 44, please delete "has" and replace therefor with --have--.

In column 2, line 52, please delete "-Trp(D)Arg" and replace therefor with ---Trp-(D)Arg--.

In column 5, line 31, please delete "compositions, Pharmaceutically" and replace therefor with --compositions. Pharmaceutically--.

In column 5, line 51, please delete "intraperitoneal" and replace therefor with --intraperitoneally--.

In column 6, line 26, please delete "(PMSF) 5mM" and replace therefor with --(PMSF), 5mM--.

In column 8, line 56, please delete "Pen2" and replace therefor with --$Pen_2$--.

UNITED STATES PATENT AND TRADEMARK OFFICE
CERTIFICATE OF CORRECTION

PATENT NO. : 5,610,271
DATED : March 11, 1997
INVENTOR(S) : Dooley et al.

It is certified that error appears in the above-identified patent and that said Letters Patent is hereby corrected as shown below:

In column 8, line 58, please delete "DPDPE." and replace therefor with --DPDPE,--.

Signed and Sealed this

Twenty-ninth Day of September, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at N- terminal."

( i x ) FEATURE:
        ( A ) NAME/KEY: Peptide
        ( B ) LOCATION: 10
        ( D ) OTHER INFORMATION: /note= "Amino acid is amidated at C- terminal."

( x i ) SEQUENCE DESCRIPTION: SEQ ID NO:1:

Tyr  Arg  Thr  Arg  Tyr  Arg  Tyr  Arg  Arg  Arg
    1                  5                                1 0

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at N- terminal."

( i x ) FEATURE:
        ( A ) NAME/KEY: Peptide
        ( B ) LOCATION: 10
        ( D ) OTHER INFORMATION: /note= "Amino acid is amidated at C- terminal."

( x i ) SEQUENCE DESCRIPTION: SEQ ID NO:2:

Tyr Arg Phe Arg Tyr Arg Tyr Arg Arg Arg
1               5                       10

( 2 ) INFORMATION FOR SEQ ID NO:3:

( i ) SEQUENCE CHARACTERISTICS:
    ( A ) LENGTH: 10 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at
          N- terminal."

( i x ) FEATURE:
    ( A ) NAME/KEY: Peptide
    ( B ) LOCATION: 10
    ( D ) OTHER INFORMATION: /note= "Amino acid is amidated at
          C- terminal."

( x i ) SEQUENCE DESCRIPTION: SEQ ID NO:3:

Arg Phe Phe Arg Tyr Arg Tyr Arg Arg Arg
1               5                       10

( 2 ) INFORMATION FOR SEQ ID NO:4:

( i ) SEQUENCE CHARACTERISTICS:
    ( A ) LENGTH: 10 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at
          N- terminal."

( i x ) FEATURE:
    ( A ) NAME/KEY: Peptide
    ( B ) LOCATION: 10
    ( D ) OTHER INFORMATION: /note= "Amino acid is amidated at
          C- terminal."

( x i ) SEQUENCE DESCRIPTION: SEQ ID NO:4:

Tyr Arg Met Arg Tyr Arg Tyr Arg Arg Arg
1               5                       10

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at
          N- terminal."

( i x ) FEATURE:
    ( A ) NAME/KEY: Peptide
    ( B ) LOCATION: 10
    ( D ) OTHER INFORMATION: /note= "Amino acid is amidated at
          C- terminal."

( x i ) SEQUENCE DESCRIPTION: SEQ ID NO:5:

Arg Arg Phe Arg Tyr Arg Tyr Arg Arg Arg
1               5                       10

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = (D)Phe"

( i x ) FEATURE:
        ( A ) NAME/KEY: Peptide
        ( B ) LOCATION: 2
        ( D ) OTHER INFORMATION: /note= "Xaa = (D)NapAla"

( i x ) FEATURE:
        ( A ) NAME/KEY: Peptide
        ( B ) LOCATION: 3
        ( D ) OTHER INFORMATION: /note= "Xaa = (D)Nle"

( i x ) FEATURE:
        ( A ) NAME/KEY: Protein
        ( B ) LOCATION: 4
        ( D ) OTHER INFORMATION: /note= "Xaa = (D)Arg"

( x i ) SEQUENCE DESCRIPTION: SEQ ID NO:6:

Xaa  Xaa  Xaa  Xaa
            1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = (D)Phe"

( i x ) FEATURE:
        ( A ) NAME/KEY: Peptide
        ( B ) LOCATION: 2
        ( D ) OTHER INFORMATION: /note= "Xaa = (D)NapAla"

( i x ) FEATURE:
        ( A ) NAME/KEY: Peptide
        ( B ) LOCATION: 3
        ( D ) OTHER INFORMATION: /note= "Xaa = (D)Nle"

( i x ) FEATURE:
        ( A ) NAME/KEY: Peptide
        ( B ) LOCATION: 4
        ( D ) OTHER INFORMATION: /note= "Xaa = (D)ChAla"

( x i ) SEQUENCE DESCRIPTION: SEQ ID NO:7:

Xaa  Xaa  Xaa  Xaa
1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = (D)Phe"

( i x ) FEATURE:
 ( A ) NAME/KEY: Peptide
 ( B ) LOCATION: 2
 ( D ) OTHER INFORMATION: /note= "Xaa = (D)NapAla"

( i x ) FEATURE:
 ( A ) NAME/KEY: Peptide
 ( B ) LOCATION: 4
 ( D ) OTHER INFORMATION: /note= "Xaa = (D)Arg"

( x i ) SEQUENCE DESCRIPTION: SEQ ID NO:8:

Xaa Xaa Trp Xaa
1

( 2 ) INFORMATION FOR SEQ ID NO:9:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
 ( A ) NAME/KEY: Peptide
 ( B ) LOCATION: 1
 ( D ) OTHER INFORMATION: /note= "Xaa = (D)Phe"

( i x ) FEATURE:
 ( A ) NAME/KEY: Peptide
 ( B ) LOCATION: 2
 ( D ) OTHER INFORMATION: /note= "Xaa = (D)NapAla"

( i x ) FEATURE:
 ( A ) NAME/KEY: Peptide
 ( B ) LOCATION: 4
 ( D ) OTHER INFORMATION: /note= "Xaa = (D)ChAla"

( x i ) SEQUENCE DESCRIPTION: SEQ ID NO:9:

Xaa Xaa Trp Xaa
1

( 2 ) INFORMATION FOR SEQ ID NO:10:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
 ( A ) NAME/KEY: Peptide
 ( B ) LOCATION: 1
 ( D ) OTHER INFORMATION: /note= "Xaa = (D)Phe"

( i x ) FEATURE:
 ( A ) NAME/KEY: Peptide
 ( B ) LOCATION: 2
 ( D ) OTHER INFORMATION: /note= "Xaa = (D)NapAla"

( i x ) FEATURE:
 ( A ) NAME/KEY: Peptide
 ( B ) LOCATION: 3
 ( D ) OTHER INFORMATION: /note= "Xaa = (D)Ile"

( i x ) FEATURE:
 ( A ) NAME/KEY: Peptide
 ( B ) LOCATION: 4
 ( D ) OTHER INFORMATION: /note= "Xaa = (D)Arg"

( x i ) SEQUENCE DESCRIPTION: SEQ ID NO:10:

Xaa Xaa Xaa Xaa
1

( 2 ) INFORMATION FOR SEQ ID NO:11:

( i ) SEQUENCE CHARACTERISTICS:

( A ) LENGTH: 4 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note= "Xaa = (D)Phe"

( i x ) FEATURE:
                    ( A ) NAME/KEY: Peptide
                    ( B ) LOCATION: 2
                    ( D ) OTHER INFORMATION: /note= "Xaa = (D)NapAla"

( i x ) FEATURE:
                    ( A ) NAME/KEY: Peptide
                    ( B ) LOCATION: 3
                    ( D ) OTHER INFORMATION: /note= "Xaa = (D)Ile"

( i x ) FEATURE:
                    ( A ) NAME/KEY: Peptide
                    ( B ) LOCATION: 4
                    ( D ) OTHER INFORMATION: /note= "Xaa = (D)ChAla"

( x i ) SEQUENCE DESCRIPTION: SEQ ID NO:11:

Xaa  Xaa  Xaa  Xaa
    1

( 2 ) INFORMATION FOR SEQ ID NO:12:

( i ) SEQUENCE CHARACTERISTICS:
                    ( A ) LENGTH: 4 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note= "Xaa = (D)Phe"

( i x ) FEATURE:
                    ( A ) NAME/KEY: Peptide
                    ( B ) LOCATION: 2
                    ( D ) OTHER INFORMATION: /note= "Xaa = (D)Phe"

( i x ) FEATURE:
                    ( A ) NAME/KEY: Peptide
                    ( B ) LOCATION: 3
                    ( D ) OTHER INFORMATION: /note= "Xaa = (D)Nle"

( i x ) FEATURE:
                    ( A ) NAME/KEY: Peptide
                    ( B ) LOCATION: 4
                    ( D ) OTHER INFORMATION: /note= "Xaa = (D)Arg"

( x i ) SEQUENCE DESCRIPTION: SEQ ID NO:12:

Xaa  Xaa  Xaa  Xaa
    1

( 2 ) INFORMATION FOR SEQ ID NO:13:

( i ) SEQUENCE CHARACTERISTICS:
                    ( A ) LENGTH: 4 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note= "Xaa = (D)Phe"

( i x ) FEATURE:
                    ( A ) NAME/KEY: Peptide
                    ( B ) LOCATION: 2
                    ( D ) OTHER INFORMATION: /note= "Xaa = (D)Phe"

( i x ) FEATURE:
    ( A ) NAME/KEY: Peptide
    ( B ) LOCATION: 3
    ( D ) OTHER INFORMATION: /note= "Xaa = (D)Nle"

( i x ) FEATURE:
    ( A ) NAME/KEY: Peptide
    ( B ) LOCATION: 4
    ( D ) OTHER INFORMATION: /note= "Xaa = (D)ChAla"

( x i ) SEQUENCE DESCRIPTION: SEQ ID NO:13:

Xaa Xaa Xaa Xaa
1

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note= "Xaa = (D)Phe"

( i x ) FEATURE:
    ( A ) NAME/KEY: Peptide
    ( B ) LOCATION: 2
    ( D ) OTHER INFORMATION: /note= "Xaa = (D)Phe"

( i x ) FEATURE:
    ( A ) NAME/KEY: Peptide
    ( B ) LOCATION: 4
    ( D ) OTHER INFORMATION: /note= "Xaa = (D)Arg"

( x i ) SEQUENCE DESCRIPTION: SEQ ID NO:14:

Xaa Xaa Trp Xaa
1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note= "Xaa = (D)Phe"

( i x ) FEATURE:
    ( A ) NAME/KEY: Peptide
    ( B ) LOCATION: 2
    ( D ) OTHER INFORMATION: /note= "Xaa = (D)Phe"

( i x ) FEATURE:
    ( A ) NAME/KEY: Peptide
    ( B ) LOCATION: 4
    ( D ) OTHER INFORMATION: /note= "Xaa = (D)ChAla"

( x i ) SEQUENCE DESCRIPTION: SEQ ID NO:15:

Xaa Xaa Trp Xaa
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:

( A ) NAME/KEY: Peptide
                    ( B ) LOCATION: 1
                    ( D ) OTHER INFORMATION: /note= "Xaa = (D)Phe"

( i x ) FEATURE:
                    ( A ) NAME/KEY: Peptide
                    ( B ) LOCATION: 2
                    ( D ) OTHER INFORMATION: /note= "Xaa = (D)Phe"

( i x ) FEATURE:
                    ( A ) NAME/KEY: Peptide
                    ( B ) LOCATION: 3
                    ( D ) OTHER INFORMATION: /note= "Xaa = (D)Ile"

( i x ) FEATURE:
                    ( A ) NAME/KEY: Peptide
                    ( B ) LOCATION: 4
                    ( D ) OTHER INFORMATION: /note= "Xaa = (D)Arg"

( x i ) SEQUENCE DESCRIPTION: SEQ ID NO:16:

Xaa  Xaa  Xaa  Xaa
        1

( 2 ) INFORMATION FOR SEQ ID NO:17:

( i ) SEQUENCE CHARACTERISTICS:
                    ( A ) LENGTH: 4 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note= "Xaa = (D)Phe"

( i x ) FEATURE:
                    ( A ) NAME/KEY: Peptide
                    ( B ) LOCATION: 2
                    ( D ) OTHER INFORMATION: /note= "Xaa = (D)Phe"

( i x ) FEATURE:
                    ( A ) NAME/KEY: Peptide
                    ( B ) LOCATION: 3
                    ( D ) OTHER INFORMATION: /note= "Xaa = (D)Ile"

( i x ) FEATURE:
                    ( A ) NAME/KEY: Peptide
                    ( B ) LOCATION: 4
                    ( D ) OTHER INFORMATION: /note= "Xaa = (D)ChAla"

( x i ) SEQUENCE DESCRIPTION: SEQ ID NO:17:

Xaa  Xaa  Xaa  Xaa
        1

( 2 ) INFORMATION FOR SEQ ID NO:18:

( i ) SEQUENCE CHARACTERISTICS:
                    ( A ) LENGTH: 4 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note= "Xaa = (D)Nle"

( i x ) FEATURE:
                    ( A ) NAME/KEY: Peptide
                    ( B ) LOCATION: 2
                    ( D ) OTHER INFORMATION: /note= "Xaa = (D)NapAla"

( i x ) FEATURE:
                    ( A ) NAME/KEY: Peptide
                    ( B ) LOCATION: 3
                    ( D ) OTHER INFORMATION: /note= "Xaa = (D)Nle"

( i x ) FEATURE:
    ( A ) NAME/KEY: Peptide
    ( B ) LOCATION: 4
    ( D ) OTHER INFORMATION: /note= "Xaa = (D)Arg"

( x i ) SEQUENCE DESCRIPTION: SEQ ID NO:18:

Xaa Xaa Xaa Xaa
1

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = (D)Nle"

( i x ) FEATURE:
        ( A ) NAME/KEY: Peptide
        ( B ) LOCATION: 2
        ( D ) OTHER INFORMATION: /note= "Xaa = (D)NapAla"

( i x ) FEATURE:
        ( A ) NAME/KEY: Peptide
        ( B ) LOCATION: 3
        ( D ) OTHER INFORMATION: /note= "Xaa = (D)Nle"

( i x ) FEATURE:
        ( A ) NAME/KEY: Peptide
        ( B ) LOCATION: 4
        ( D ) OTHER INFORMATION: /note= "Xaa = (D)ChAla"

( x i ) SEQUENCE DESCRIPTION: SEQ ID NO:19:

Xaa Xaa Xaa Xaa
1

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = (D)Nle"

( i x ) FEATURE:
        ( A ) NAME/KEY: Peptide
        ( B ) LOCATION: 2
        ( D ) OTHER INFORMATION: /note= "Xaa = (D)NapAla"

( i x ) FEATURE:
        ( A ) NAME/KEY: Peptide
        ( B ) LOCATION: 4
        ( D ) OTHER INFORMATION: /note= "Xaa = (D)Arg"

( x i ) SEQUENCE DESCRIPTION: SEQ ID NO:20:

Xaa Xaa Trp Xaa
1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:

(A) NAME/KEY: Peptide
                (B) LOCATION: 1
                (D) OTHER INFORMATION: /note= "Xaa = (D)Nle"

(ix) FEATURE:
                (A) NAME/KEY: Peptide
                (B) LOCATION: 2
                (D) OTHER INFORMATION: /note= "Xaa = (D)NapAla"

(ix) FEATURE:
                (A) NAME/KEY: Peptide
                (B) LOCATION: 3
                (D) OTHER INFORMATION: /note= "Xaa = (D)Ile"

(ix) FEATURE:
                (A) NAME/KEY: Peptide
                (B) LOCATION: 4
                (D) OTHER INFORMATION: /note= "Xaa = (D)Arg"

(xi) SEQUENCE DESCRIPTION: SEQ ID NO:21:

Xaa  Xaa  Xaa  Xaa
    1

(2) INFORMATION FOR SEQ ID NO:22:

(i) SEQUENCE CHARACTERISTICS:
            (A) LENGTH: 4 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "Xaa = (D)Nle"

(ix) FEATURE:
            (A) NAME/KEY: Peptide
            (B) LOCATION: 2
            (D) OTHER INFORMATION: /note= "Xaa = (D)NapAla"

(ix) FEATURE:
            (A) NAME/KEY: Peptide
            (B) LOCATION: 3
            (D) OTHER INFORMATION: /note= "Xaa = (D)Ile"

(ix) FEATURE:
            (A) NAME/KEY: Peptide
            (B) LOCATION: 4
            (D) OTHER INFORMATION: /note= "Xaa = (D)ChAla"

(xi) SEQUENCE DESCRIPTION: SEQ ID NO:22:

Xaa  Xaa  Xaa  Xaa
    1

(2) INFORMATION FOR SEQ ID NO:23:

(i) SEQUENCE CHARACTERISTICS:
            (A) LENGTH: 4 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "Xaa = (D)Nle"

(ix) FEATURE:
            (A) NAME/KEY: Peptide
            (B) LOCATION: 2
            (D) OTHER INFORMATION: /note= "Xaa = (D)Phe"

(ix) FEATURE:
            (A) NAME/KEY: Peptide
            (B) LOCATION: 3
            (D) OTHER INFORMATION: /note= "Xaa = (D)Nle"

( i x ) FEATURE:
  ( A ) NAME/KEY: Peptide
  ( B ) LOCATION: 4
  ( D ) OTHER INFORMATION: /note= "Xaa = (D)Arg"

( x i ) SEQUENCE DESCRIPTION: SEQ ID NO:23:

Xaa Xaa Xaa Xaa
1

( 2 ) INFORMATION FOR SEQ ID NO:24:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "Xaa = (D)Nle"

( i x ) FEATURE:
  ( A ) NAME/KEY: Peptide
  ( B ) LOCATION: 2
  ( D ) OTHER INFORMATION: /note= "Xaa = (D)Phe"

( i x ) FEATURE:
  ( A ) NAME/KEY: Peptide
  ( B ) LOCATION: 4
  ( D ) OTHER INFORMATION: /note= "Xaa = (D)Arg"

( x i ) SEQUENCE DESCRIPTION: SEQ ID NO:24:

Xaa Xaa Trp Xaa
1

( 2 ) INFORMATION FOR SEQ ID NO:25:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "Xaa = (D)Nle"

( i x ) FEATURE:
  ( A ) NAME/KEY: Peptide
  ( B ) LOCATION: 2
  ( D ) OTHER INFORMATION: /note= "Xaa = (D)Phe"

( i x ) FEATURE:
  ( A ) NAME/KEY: Peptide
  ( B ) LOCATION: 4
  ( D ) OTHER INFORMATION: /note= "Xaa = (D)ChAla"

( x i ) SEQUENCE DESCRIPTION: SEQ ID NO:25:

Xaa Xaa Trp Xaa
1

( 2 ) INFORMATION FOR SEQ ID NO:26:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "Xaa = (D)Nle"

( i x ) FEATURE:

(A) NAME/KEY: Peptide
(B) LOCATION: 2
(D) OTHER INFORMATION: /note= "Xaa = (D)Phe"

(ix) FEATURE:
(A) NAME/KEY: Peptide
(B) LOCATION: 3
(D) OTHER INFORMATION: /note= "Xaa = (D)Ile"

(ix) FEATURE:
(A) NAME/KEY: Peptide
(B) LOCATION: 4
(D) OTHER INFORMATION: /note= "Xaa = (D)Arg"

(xi) SEQUENCE DESCRIPTION: SEQ ID NO:26:

Xaa Xaa Xaa Xaa
1

(2) INFORMATION FOR SEQ ID NO:27:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Xaa = (D)Nle"

(ix) FEATURE:
(A) NAME/KEY: Peptide
(B) LOCATION: 2
(D) OTHER INFORMATION: /note= "Xaa = (D)Phe"

(ix) FEATURE:
(A) NAME/KEY: Peptide
(B) LOCATION: 3
(D) OTHER INFORMATION: /note= "Xaa = (D)Ile"

(ix) FEATURE:
(A) NAME/KEY: Peptide
(B) LOCATION: 4
(D) OTHER INFORMATION: /note= "Xaa = (D)ChAla"

(xi) SEQUENCE DESCRIPTION: SEQ ID NO:27:

Xaa Xaa Xaa Xaa
1

(2) INFORMATION FOR SEQ ID NO:28:

(i) SEQUENCE CHARACTERISTICS:
(A) LENGTH: 10 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Amino acid is acetylated at
N- terminal"

(ix) FEATURE:
(A) NAME/KEY: Peptide
(B) LOCATION: 1
(D) OTHER INFORMATION: /note= "Xaa = A1, wherein A1 is Tyr
or Arg"

(ix) FEATURE:
(A) NAME/KEY: Peptide
(B) LOCATION: 2
(D) OTHER INFORMATION: /note= "Xaa = B2, wherein B2 is Arg
or Phe"

(ix) FEATURE:
(A) NAME/KEY: Peptide (B) LOCATION: 3
(D) OTHER INFORMATION: /note= "Xaa = C3, wherein C3 is
Thr, Phe or Met"

(ix) FEATURE:
(A) NAME/KEY: Peptide
(B) LOCATION: 10
(D) OTHER INFORMATION: /note= "Amino acid is amidated at
C- terminal."

(xi) SEQUENCE DESCRIPTION: SEQ ID NO:28:

Xaa Xaa Xaa Arg Tyr Arg Tyr Arg Arg Arg
1               5                   10

(2) INFORMATION FOR SEQ ID NO:29:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Xaa = (D)Phe"

(ix) FEATURE:
(A) NAME/KEY: Peptide
(B) LOCATION: 2
(D) OTHER INFORMATION: /note= "Xaa = D4, wherein D4 is
(D)NapAla or (D)Phe"

(ix) FEATURE:
(A) NAME/KEY: Peptide
(B) LOCATION: 3
(D) OTHER INFORMATION: /note= "Xaa = E5, wherein E5 is
(D)Nle, Trp or (D)Ile"

(ix) FEATURE:
(A) NAME/KEY: Peptide
(B) LOCATION: 4
(D) OTHER INFORMATION: /note= "Xaa = F6, wherein F6 is
(D)Arg or (D)ChAla"

(xi) SEQUENCE DESCRIPTION: SEQ ID NO:29:

Xaa Xaa Xaa Xaa
1

(2) INFORMATION FOR SEQ ID NO:30:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Xaa = (D)Nle"

(ix) FEATURE:
(A) NAME/KEY: Peptide
(B) LOCATION: 2
(D) OTHER INFORMATION: /note= "Xaa = D4, wherein D4 is
(D)NapAla or (D)Phe"

(ix) FEATURE:
(A) NAME/KEY: Peptide
(B) LOCATION: 3
(D) OTHER INFORMATION: /note= "Xaa = E5, wherein E5 is
(D)Nle, Trp or (D)Ile"

(ix) FEATURE:
(A) NAME/KEY: Peptide
(B) LOCATION: 4
(D) OTHER INFORMATION: /note= "Xaa = F6, wherein F6 is (D)Arg or (D)ChAla"

(xi) SEQUENCE DESCRIPTION: SEQ ID NO:30:

Xaa Xaa Xaa Xaa
1